US009597025B2

United States Patent
Kobayashi et al.

(10) Patent No.: US 9,597,025 B2
(45) Date of Patent: Mar. 21, 2017

(54) BIOLOGICAL SIGNAL MEASURING SYSTEM AND BIOLOGICAL SIGNAL MEASURING APPARATUS

(71) Applicant: NIHON KOHDEN CORPORATION, Tokyo (JP)

(72) Inventors: Naoki Kobayashi, Tokyo (JP); Hideaki Hirabara, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/286,426

(22) Filed: May 23, 2014

(65) Prior Publication Data

US 2014/0371557 A1  Dec. 18, 2014

(30) Foreign Application Priority Data

Jun. 13, 2013  (JP) .................................. 2013-124830

(51) Int. Cl.
  *A61B 5/1455* (2006.01)
  *A61B 5/00* (2006.01)
  *G01N 21/31* (2006.01)

(52) U.S. Cl.
  CPC ........ *A61B 5/14552* (2013.01); *A61B 5/6826* (2013.01); *A61B 5/7203* (2013.01);
  (Continued)

(58) Field of Classification Search
  CPC .............. A61B 5/1455; A61B 5/14551; A61B 5/14552; A61B 5/72; A61B 5/7271; A61B 5/7278
  See application file for complete search history.

(56) References Cited

U.S. PATENT DOCUMENTS 4,883,055 A * 11/1989 Merrick ............. A61B 5/14552
  600/335
5,522,388 A *  6/1996 Ishikawa ............ A61B 5/14551
  600/322

(Continued)

FOREIGN PATENT DOCUMENTS

JP  2002-228579 A   8/2002
JP  2003-532107 A  10/2003

(Continued)

OTHER PUBLICATIONS

The extended European Search Report for the related European Patent Application No. 14167610.6 dated Oct. 21, 2014.

(Continued)

*Primary Examiner* — Eric Winakur
(74) *Attorney, Agent, or Firm* — Pearne & Gordon LLP

(57) ABSTRACT

A biological signal measuring system includes: a light emitter emitting light beams having different N kinds of wavelengths, where N is an integer of four or more; a light receiver outputting N kinds of signals respectively in accordance with received light intensities of the N kinds of light beams that have been passed through or reflected from a living tissue; a first calculating section acquiring N kinds of light attenuations based on the N kinds of signals; a second calculating section acquiring (N−1) kinds of blood-derived light attenuations based on two light attenuations related to (N−1) kinds of combinations selected from the N kinds of light attenuations; a third calculating section identifying concentrations of (N−1) kinds of in-blood substances based on the (N−1) kinds of blood-derived light attenuations; and an outputting section outputting the identified concentrations.

16 Claims, 6 Drawing Sheets

(52) U.S. Cl.
CPC ......... *A61B 5/7271* (2013.01); *G01N 21/314* (2013.01); *A61B 2505/01* (2013.01); *A61B 2505/03* (2013.01); *G01N 2021/3144* (2013.01); *G01N 2021/3148* (2013.01)

(56) References Cited

U.S. PATENT DOCUMENTS

| | | | |
|---|---|---|---|
| 5,692,503 A | 12/1997 | Kuenstner | |
| 5,720,284 A * | 2/1998 | Aoyagi | A61B 5/14551 600/322 |
| 6,149,588 A * | 11/2000 | Noda | A61B 5/14532 600/316 |
| 6,151,518 A | 11/2000 | Hayashi | |
| 6,285,894 B1 * | 9/2001 | Oppelt | A61B 5/14532 600/310 |
| 6,587,704 B1 | 7/2003 | Fine et al. | |
| 7,003,337 B2 * | 2/2006 | Harjunmaa | A61B 5/14532 600/310 |
| 7,613,488 B1 * | 11/2009 | Maracas | A61B 5/14532 600/322 |
| 7,672,702 B2 * | 3/2010 | Hwang | A61B 5/14532 600/316 |
| 2001/0047128 A1 | 11/2001 | Benni | |
| 2002/0111748 A1 | 8/2002 | Kobayashi et al. | |
| 2004/0024297 A1 | 2/2004 | Chen et al. | |
| 2006/0189861 A1 | 8/2006 | Chen et al. | |
| 2012/0108927 A1 | 5/2012 | Chen et al. | |

FOREIGN PATENT DOCUMENTS

| | | |
|---|---|---|
| JP | 2005-533609 A | 11/2005 |
| JP | 2006-075354 A | 3/2006 |

OTHER PUBLICATIONS

Japanese Office Action issued in Patent Application No. JP 2013-124830 dated Jan. 31, 2017.

\* cited by examiner

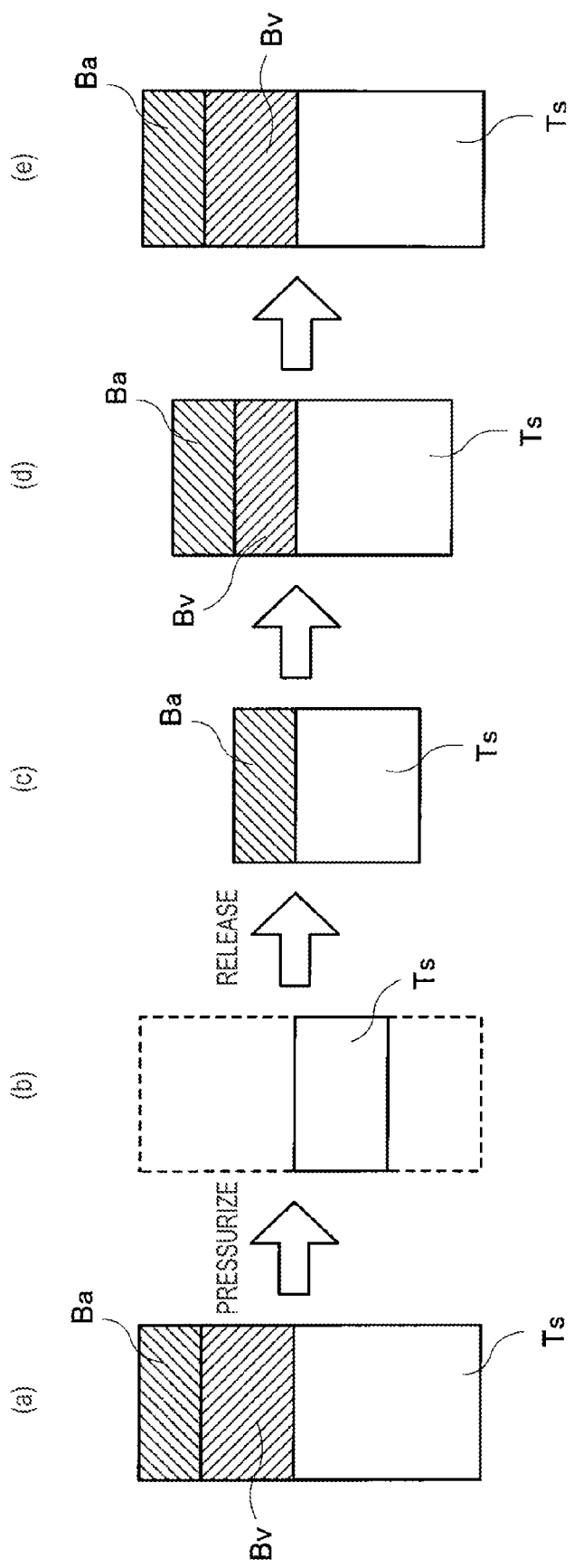

BIOLOGICAL SIGNAL MEASURING SYSTEM AND BIOLOGICAL SIGNAL MEASURING APPARATUS

CROSS-REFERENCE TO RELATED APPLICATION(S)

This application is based upon and claims the benefit of priority from prior Japanese patent application No. 2013-124830, filed on Jun. 13, 2013, the entire contents of which are incorporated herein by reference.

BACKGROUND

The presently disclosed subject matter relates to a biological signal measuring system, and more particularly to a system for identifying the concentration of a substance in blood (hereinafter, such a substance is referred to as "in-blood substance") based on a biological signal acquired from a subject that is an example of the living body. The presently disclosed subject matter relates also to a biological signal measuring apparatus which is to be used in the system.

Measurement of the degree of oxygenation of blood is important for determining whether blood is sufficiently supplied to the living tissue or not. The degree of oxygenation of arterial blood, i.e., the arterial oxygen saturation can be easily measured by using a pulse oximeter. There is also a method of measuring the blood concentration of carbon monoxide hemoglobin COHb or methemoglobin MetHb, which is abnormal hemoglobin, by using the principle of the pulse oximeter (for example, see JP-A-2002-228579).

When the principle of the pulse oximeter is used, non-invasive measurement can be easily performed, but the pulse wave amplitude depends on the measurement accuracy. In the case where a disorder occurs in the circulation and the pulse wave extremely weakens, for example, the measurement is disabled. In the case of carbon monoxide poisoning, when the COHb concentration exceeds 50%, the cardiac function is lowered and comatose is caused. Also in such a case, measurement based on the principle of the pulse oximeter is sometimes impossible.

SUMMARY

The presently disclosed subject matter may provide a technique in which, even from a patient who is in a comatose state and whose circulation is impaired, information related to the concentrations of in-blood substances is acquired by a simple method.

There may be provided a biological signal measuring system comprising: a light emitter which is configured to emit light beams having different N kinds of wavelengths, where N is an integer of four or more; a light receiver which is configured to output N kinds of signals respectively in accordance with received light intensities of the N kinds of light beams that have been passed through or reflected from a living tissue of a subject; a first calculating section which is configured to acquire N kinds of light attenuations based on the N kinds of signals; a second calculating section which is configured to acquire (N−1) kinds of blood-derived light attenuations based on two light attenuations related to (N−1) kinds of combinations selected from the N kinds of light attenuations; a third calculating section which is configured to identify concentrations of (N−1) kinds of in-blood substances based on the (N−1) kinds of blood-derived light attenuations; and an outputting section which is configured to output the identified concentrations.

The second calculating section may acquire each of the blood-derived light attenuations based on a difference of the two light attenuations.

Two wavelengths corresponding to the two light attenuations which are used for acquiring the difference may be selected as wavelengths in which a difference of light attenuations of non-blood tissue is smaller, from the N kinds of wavelengths.

The difference may be obtained by multiplying by a coefficient corresponding to the light attenuation of non-blood tissue in the corresponding wavelength.

The N may be four, and the in-blood substances may be three kinds selected from oxygenated hemoglobin, reduced hemoglobin, carbon monoxide hemoglobin, and methemoglobin.

The N may be five, and the in-blood substances may be oxygenated hemoglobin, reduced hemoglobin, carbon monoxide hemoglobin, and methemoglobin.

The biological signal measuring system may further comprise a monitoring section which is configured to cause the third calculating section to identify the concentrations at a predetermined timing.

The monitoring section may notify a timing when the living tissue is to be pressed, through the outputting section.

The biological signal measuring system may further comprise a pressure detecting section which is configured to detect a pressure applied to the living tissue, and which is configured to output a signal corresponding to the pressure.

The light attenuations may be acquired based on changes of the received light intensities due to pressing of the living tissue.

The biological signal measuring system may further comprise: a pressurizing section which is adapted to be attached to the subject so as to pressurize the living tissue; and a pressurization controlling section which is configured to control the pressurizing section for causing changes of light attenuations of the living tissue.

There may be provided a biological signal measuring apparatus comprising: a signal receiving section which is configured to receive N kinds of signals corresponding to light intensities of light beams that have been passed through or reflected from a living tissue of a subject and that have N kinds of wavelengths, where N is an integer of four or more; a first calculating section which is configured to acquire N kinds of light attenuations based on the N kinds of signals; a second calculating section which is configured to acquire (N−1) kinds to of blood-derived light attenuations based on two light attenuations related to (N−1) kinds of combinations selected from the N kinds of light attenuations; a third calculating section which is configured to identify concentrations of (N−1) kinds of in-blood substances based on the (N−1) kinds of blood-derived light attenuations; and an outputting section which is configured to output the identified concentrations.

There may be provided a method of controlling a biological signal measuring apparatus comprising a signal receiving section which is configured to receive N kinds of signals corresponding to light intensities of light beams that have been passed through or reflected from a living tissue of a subject and that have N kinds of wavelengths, where N is an integer of four or more, the method comprising: acquiring N kinds of light attenuations based on the N kinds of signals; acquiring (N−1) kinds of blood-derived light attenuations based on two light attenuations related to (N−1) kinds of combinations selected from the N kinds of light attenuations; identifying concentrations of (N−1) kinds of in-blood substances based on the (N−1) kinds of blood-derived light attenuations, and outputting the identified concentrations.

There may be provided a program causing a computer to execute the method.

There may be provided a non-transitory computer-readable recording medium storing a program causing a computer to execute the method.

BRIEF DESCRIPTION OF THE DRAWINGS

FIG. 5 is a diagram illustrating identification of the concentration of the in-blood substance associated with pressurization of a living tissue.

DETAILED DESCRIPTION OF EXEMPLARY EMBODIMENTS

Figure 1:
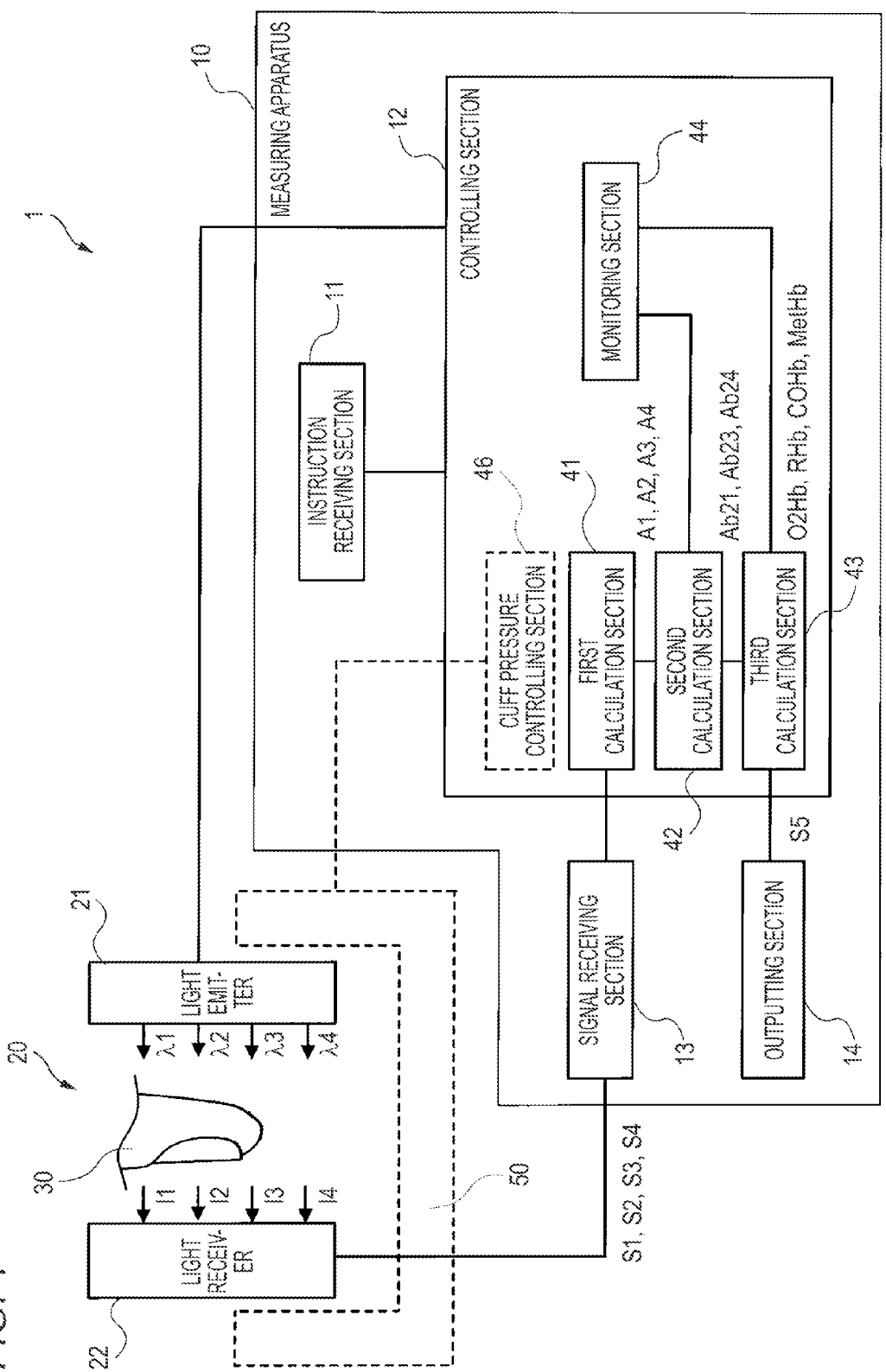
FIG. 1 is a functional block diagram showing the configuration of a biological signal measuring system of an embodiment of the presently disclosed subject matter.

An embodiment of the presently disclosed subject matter will be described in detail with reference to the accompanying drawings. In the drawings which will be used in the following description, the scale is adequately changed in order to draw components in a recognizable size.

As shown in FIG. 1, a biological signal measuring system 1 of the embodiment includes a measuring apparatus 10 and a probe 20. The measuring apparatus 10 includes an instruction receiving section 11, a controlling section 12, a signal receiving section 13, and an outputting section 14. The probe 20 in the embodiment has a configuration which is to be attached to the finger 30 of the subject, and includes a light emitter 21 and a light receiver 22.

The instruction receiving section 11 is a man-machine interface which is disposed on the outer surface of the measuring apparatus 10, and configured so as to be able to receive instructions which are input by the user in order to cause the measuring apparatus 10 to perform a desired operation.

The controlling section 12 includes: a CPU which performs various calculation processes; a ROM which stores various control programs; a RAM which is used as a working area for storing data and executing the programs; and the like, and performs various controls in the measuring apparatus 10. The controlling section 12 is communicably connected to the instruction receiving section 11. The instruction receiving section 11 supplies a signal corresponding to the received instructions, to the controlling section 12.

The light emitter 21 of the probe 20 is communicably connected to the controlling section 12 of the measuring apparatus 10. The light emitter 21 can emit a first light beam having a first wavelength $\lambda 1$, a second light beam having a second wavelength $\lambda 2$, a third light beam having a third wavelength $\lambda 3$, and a fourth light beam having a fourth wavelength $\lambda 4$.

In the embodiment, the light emitter 21 includes a light emitting diode which emits a red light beam of 660 nm that is an example of the first wavelength $\lambda 1$, another light emitting diode which emits an infrared light beam of 940 nm that is an example of the second wavelength $\lambda 2$, a further light emitting diode which emits an infrared light beam of 810 nm that is an example of the third wavelength $\lambda 3$, and a still further light emitting diode which emits a red light beam of 620 nm or 635 nm that is an example of the fourth wavelength $\lambda 4$. In accordance with a control signal supplied from the controlling section 12, each of the light emitting diodes emits the light beam at predetermined timings. The emitted first, second, third, and fourth light beams enter the finger 30 which is an example of the living tissue.

The light receiver 22 of the probe 20 is placed at a position where the first, second, third, and fourth light beams which have been passed through the finger 30 can be received. The light receiver 22 is configured so as to be able to output a first signal S1 corresponding to the intensity I1 of the received first light beam, a second signal S2 corresponding to the intensity I2 of the received second light beam, a third signal S3 corresponding to the intensity I3 of the received third light beam, and a fourth signal S4 corresponding to the intensity I4 of the received fourth light beam.

In the embodiment, photodiodes are used as devices having such a configuration. The light receiver 22 is communicably connected to the signal receiving section 13 of the measuring apparatus 10. The signals S1, S2, S3, S4 which are output from the light receiver 22 are supplied to the signal receiving section 13.

The signal receiving section 13 is communicably connected to the controlling section 12. The signal receiving section 13 supplies the received signals S1, S2, S3, S4 to the controlling section 12. The controlling section 12 includes a first calculating section 41, a second calculating section 42, a third calculating section 43, and a monitoring section 44.

The first calculating section 41 is configured so as to acquire the light attenuation A1 of the first light beam based on the first signal S1, the light attenuation A2 of the second light beam based on the second signal S2, the light attenuation A3 of the third light beam based on the third signal S3, and the light attenuation A4 of the fourth light beam based on the fourth signal S4. Each of the light attenuations A1, A2, A3, A4 is calculated as a ratio of the amount of light of the first, second, third, or fourth signal S1, S2, S3, or S4 received at a certain time (for example, during pressurization of the living tissue) to that at another time (for example, before pressurization of the living tissue), and indicated by either of the following expressions:

$$A1 = \log(I1/Io1) \tag{1}$$

$$A2 = \log(I2/Io2) \tag{2}$$

$$A3 = \log(I3/Io3) \tag{3}$$

$$A4 = \log(I4/Io4) \tag{4}$$

where Io1, Io2, Io3, and Io4 indicate the amounts of received light at the reference time (for example, before pressurization of the living tissue), and I1, I2, I3, and I4 indicate the amounts of received light at the measurement. The suffix "1" indicates the first light beam, the suffix "2" indicates the second light beam, the suffix "3" indicates the third light beam, and the suffix "4" indicates the fourth light beam.

The second calculating section 42 is configured so as to acquire blood-derived light attenuations based on the light attenuations A1, A2 of the first and second light beams acquired by the first calculating section 41, the light attenuations A2, A3 of the second and third light beams, and the light attenuations A2, A4 of the second and fourth light beams. Specifically, the section is configured so as to acquire the blood-derived light attenuation Ab21 based on the difference of the light attenuation A1 and the light attenuation A2, the blood-derived light attenuation Ab23 based on the difference of the light attenuation A2 and the light attenuation A3, and the blood-derived light attenuation Ab24 based on the difference of the light attenuation A2 and the light attenuation A4. The principle of the process will be described in detail below.

A change A in light attenuation which is produced when the finger 30 is pressed to change the thickness of the living tissue is caused by a change in thickness of blood and that in thickness of tissue other than blood (hereinafter, such tissue is referred to as non-blood tissue). This fact is indicated by the following expressions:

$$A1 = Ab1 + At1 = E1HbDb + Z1Dt \quad (5)$$

$$A2 = Ab2 + At2 = E2HbDb + Z2Dt \quad (6)$$

$$A3 = Ab3 + At3 = E3HbDb + Z3Dt \quad (7)$$

$$A4 = Ab4 + At4 = E4HbDb + Z4Dt \quad (8)$$

where E indicates the absorption coefficient (dl g$^{-1}$cm$^{-1}$), Hb indicates the hemoglobin concentration (g dl$^{-1}$), Z indicates the light attenuation factor (cm$^{-1}$) of the non-blood tissue, and D indicates the thickness (cm). The suffix "b" indicates blood, the suffix "t" indicates the non-blood tissue, the suffix "1" indicates the first light beam, the suffix "2" indicates the second light beam, the suffix "3" indicates the third light beam, and the suffix "4" indicates the fourth light beam.

The wavelength dependency of the non-blood tissue can be neglected. Therefore, it can be deemed that Z1=Z2=Z3=Z4. When Expression (5) is subtracted from Expression (6), Expression (7) is subtracted from Expression (6), and Expression (8) is subtracted from Expression (6), the following expressions are obtained:

$$Ab21 = A2 - A1 = (E2 - E1)HbDb \quad (9)$$

$$Ab23 = A2 - A3 = (E2 - E3)HbDb \quad (10)$$

$$Ab24 = A2 - A4 = (E2 - E4)HbDb \quad (11)$$

The right side contains only information of blood. When the difference of the light attenuation A2 and the light attenuation A1, that of the light attenuation A2 and the light attenuation A3, and that of the light attenuation A2 and the light attenuation A4 are obtained, therefore, it is possible to acquire the blood-derived light attenuations Ab21, Ab23, and Ab24.

Next, Expression (9) is divided by Expression (10), and Expression (9) is divided by Expression (11), the terms of Hb and Db are deleted, and the following expressions are obtained:

$$Ab21/Ab23 = (A2 - A1)/(A2 - A3) = (E2 - E1)/(E2 - E3) \quad (12)$$

$$Ab21/Ab24 = (A2 - A1)/(A2 - A4) = (E2 - E1)/(E2 - E4) \quad (13)$$

In Expressions (12) and (13), (E2−E1), (E2−E3), and (E2−E4) are functions of the oxygenated hemoglobin concentration O2Hb (%), the reduced hemoglobin concentration RHb (%), and the carbon monoxide hemoglobin concentration COHb (%). The absorption coefficients E1, E2, E3, and E4 are expressed by the following expressions:

$$E1 = Eo1 \cdot O2Hb + Er1 \cdot RHb + Ec1 \cdot COHb \quad (14)$$

$$E2 = Eo2 \cdot O2Hb + Er2 \cdot RHb + Ec2 \cdot COHb \quad (15)$$

$$E3 = Eo3 \cdot O2Hb + Er3 \cdot RHb + Ec3 \cdot COHb \quad (16)$$

$$E4 = Eo4 \cdot O2Hb + Er4 \cdot RHb + Ec4 \cdot COHb \quad (16)$$

$$O2Hb + RHb + COHb = 1 \quad (17)$$

where Eo indicates the absorption coefficient of oxygenated hemoglobin, Er indicates the absorption coefficient of reduced hemoglobin, and Ec indicates the absorption coefficient of carbon monoxide hemoglobin. The suffix "1" indicates the first light beam, the suffix "2" indicates the second light beam, the suffix "3" indicates the third light beam, and he suffix "4" indicates the fourth light beam.

Figure 2:
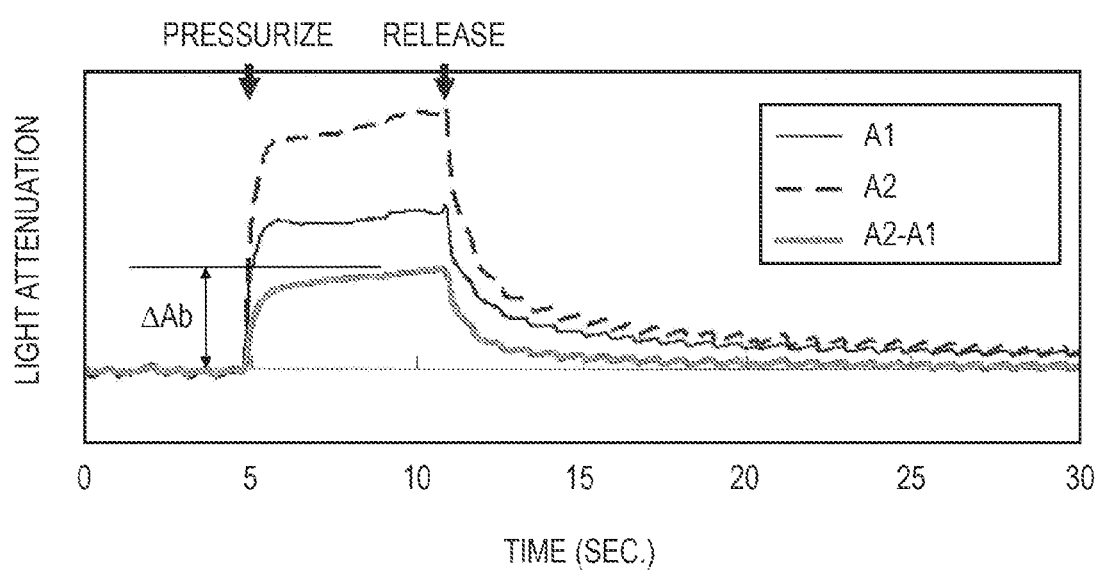
FIG. 2 is a view illustrating an example of a process which is performed by a second calculating section of the biological signal measuring system.

Hereinafter, the meaning of the acquisition of the difference of light attenuations will be described with reference to FIG. 2. FIG. 2 shows a graph showing temporal changes of the light attenuation A1, the light attenuation A2, and the blood-derived light attenuation Ab21 (=A2−A1) in the case where the finger 30 is pressed through the probe 20.

It is seen that, even when the pressurization is released, the values of the light attenuations A1, A2 do not return to the levels which are attained before the start of the pressurization, and the deformation of the non-blood tissue exerts influence. It is also seen that, after the release of the pressurization, the difference (A2−A1) of the light attenuations, i.e., the blood-derived light attenuation Ab21 converges to the level which is attained before the start of the pressurization. Namely, the influence caused by the deformation of the non-blood tissue can be eliminated by a simple calculation process in which the difference of the light attenuations that are obtained by irradiating the tissue with light beams of different wavelengths is calculated.

Figure 3:
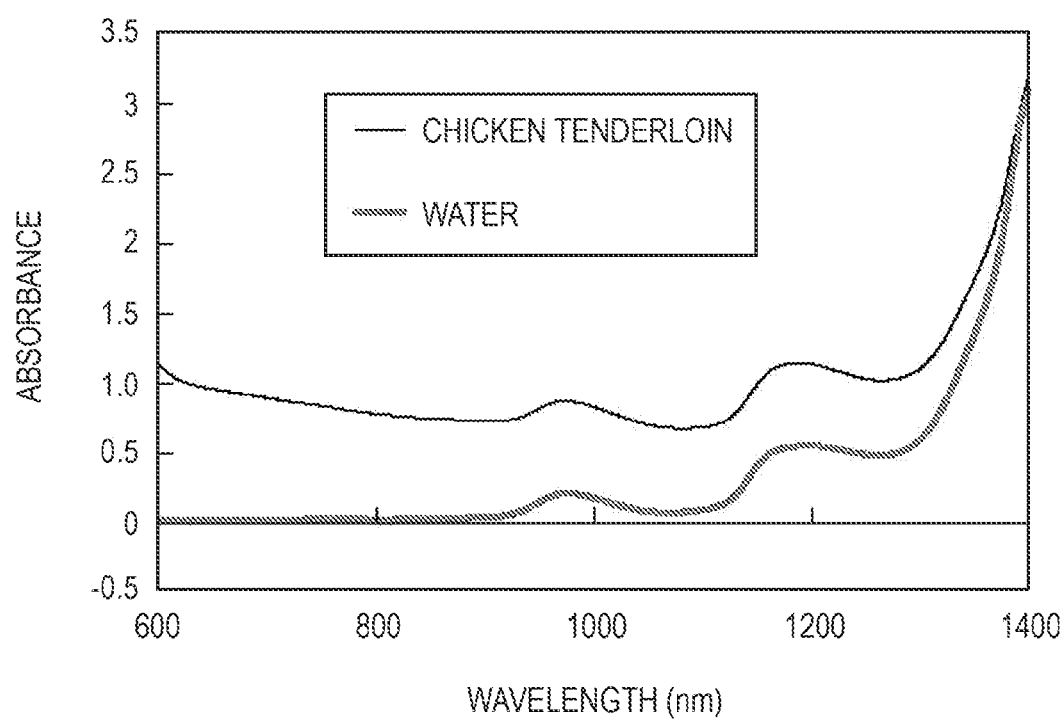
FIG. 3 is a view of complementing the illustration of the process which is performed by the second calculating section.

As described above, the wavelength dependency of the non-blood tissue can be neglected. However, exact equality is not attained. FIG. 3 shows optical absorption spectra of bloodless chicken tenderloin and water. In the range of 600 to 1,100 nm, the absorbance of the chicken tenderloin is substantially constant, but the light attenuation of short wavelength light is larger than that of long wavelength light. In the above-described subtraction, therefore, the influence of the non-blood tissue can be further reduced in the case where subtraction of light attenuations acquired from a wavelength at which the difference of light attenuations of non-blood tissues is smaller is performed, and hence the concentration of the in-blood substance can be correctly calculated. In the case where subtraction is performed by using values at 810 nm and 940 nm, for example, the influence of the non-blood tissue can be reduced further than the case where subtraction is performed by using values at 660 nm and 940 nm.

Although, as described above, there is a small difference in the light attenuation of the non-blood tissue depending on the wavelength, the influence of the tissue can be strictly eliminated. In the case where the light attenuation factors of the non-blood tissue at the wavelengths have relationships of Z2=k2Z1, Z3=k3Z1, and Z4=k4Z1, when subtraction is performed after multiplying by a constant k as follows:

$$A1 = Ab1 + At1 = E1HbDb + Z1Dt \quad (18)$$

$$k2A2 = k2Ab2 + k2At2 = k2E2HbDb + k2Z2Dt \quad (19)$$

$$k3A3=k3Ab3+k3At3=k3E3HbDb+k3Z3Dt \quad (20)$$

$$k4A4=k4Ab4+k4At4=k4E4HbDb+k3Z4Dt \quad (21),$$

the terms of the light attenuations of the non-blood tissue are completely eliminated, and therefore a measurement which is errorless and more accurate is enabled. The coefficients k2, k3, and k4 can be previously determined by a measurement such as that of FIG. 3.

Figure 4A:
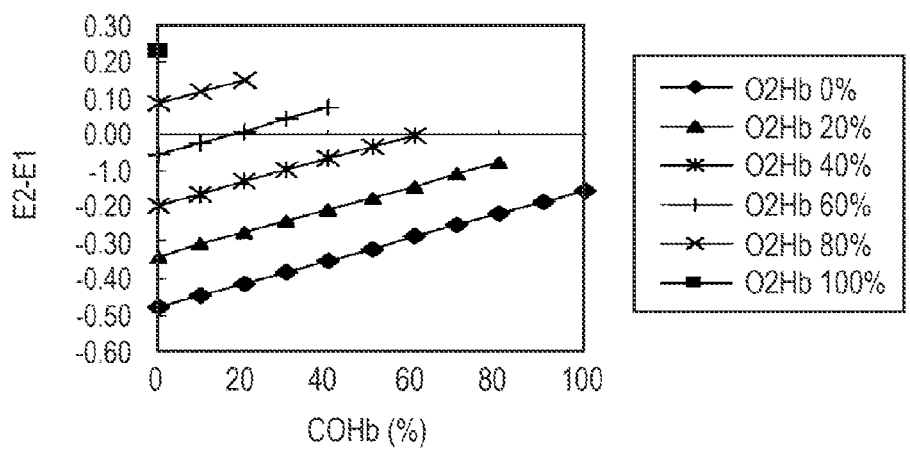
FIGS. 4A to 4C are views illustrating relationships between the absorption coefficient and the concentration of an in-blood substance.
Figure 4B:
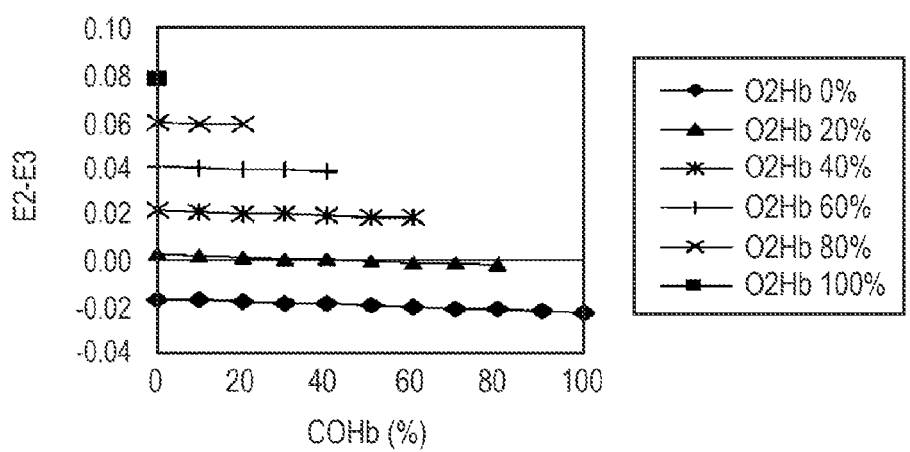
Figure 4C:
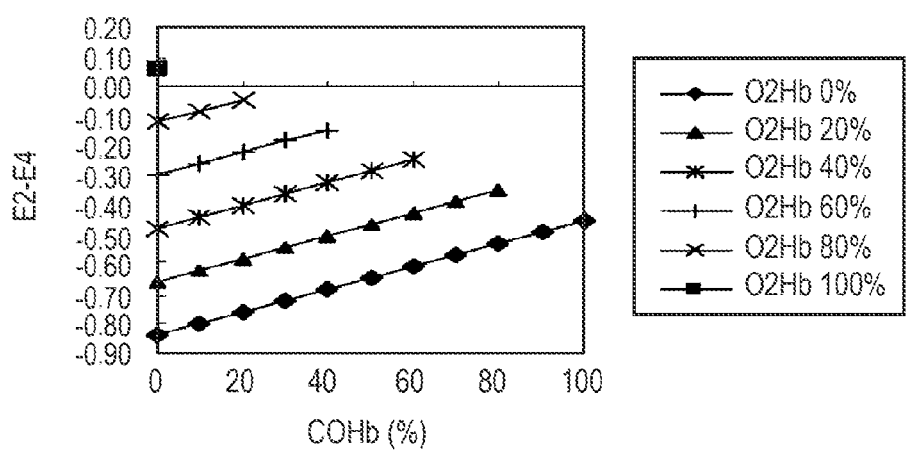

FIGS. 4A to 4C show relationships between (E2−E1), (E2−E3), and (E2−E4) above and the O2Hb concentration, the RHb concentration, and the COHb concentration in the case where three kinds of hemoglobins, or O2Hb, RHb, and COHb are in the blood. Since (E2−E1), (E2−E3), and (E2−E4) are functions of the O2Hb, RHb, and COHb concentrations, the left sides of Expressions (12) and (13) which are measurement values are functions of the O2Hb, RHb, and COHb concentrations. Although the RHb concentration is not directly described in the figures, the RHb concentration has a value which is obtained by subtracting the sum of the O2Hb and COHb concentrations from 100%.

From the above, it is seen that, when the blood-derived light attenuations Ab21, Ab23, and Ab24 are measured by using light beams having at least four kinds of wavelengths, the O2Hb, RHb, and COHb concentrations in the blood can be Quantitatively identified through Expressions (12) to (17). The third calculating section 43 is configured so as to identify the O2Hb, RHb, and COHb concentrations based on the principle. Also in the case where MetHb is used in placed of COHb, similar measurements can be performed.

The controlling section 12 supplies a signal S5 indicative of a result of the determination which is performed by the third calculating section 43, to the outputting section 14. The outputting section 14 is a man-machine interface which is disposed on the outer surface of the measuring apparatus 10, and includes a displaying device which displays visible information. The displaying device displays the determination result in an adequate manner corresponding to the signal S5.

According to the configuration of the embodiment, therefore, the concentrations of the in-blood substances can be identified only by attaching the probe 20 for pulse oximetry in which measurement is conducted by using four or more wavelengths, to the finger 30 of the subject. In a scene of first aid, for example, the concentrations of in-blood substances can be identified simply and rapidly by using a multi-wavelength pulse oximeter and without requiring preparation of a special probe and performing a special work. This can contribute to rapid determination of the priority.

When five wavelengths are used, it is possible to obtain four kinds of hemoglobin concentrations. For example, the O2Hb concentration, the RHb concentration, the COHb concentration, and the MetHb concentration can be simultaneously obtained. In the case where the fourth wavelength λ4 is one of 620 nm and 635 nm, an example of the fifth wavelength λ5 is the other of the frequencies.

According to the configuration of the embodiment, the concentrations of in-blood substances can be identified only by attaching the probe 20 for pulse oximetry in which measurement is conducted by using five or more wavelengths, to the finger 30 of the subject. Even from a patient who is in a comatose state and whose circulation is impaired, for example, information related to the concentrations of the in-blood substances can be acquired by attaching a multi-wavelength pulse oximeter to the patient and without requiring preparation of a special probe and performing a special work.

According to the embodiment, the dye dilution method can be performed. The dye dilution method is a method in which, after a dye is administered to blood, the blood dye concentration is measured, and the circulatory function or the liver function is evaluated. As the dye, for example, indocyanine green is used.

The monitoring section 44 is configured so as to perform a monitoring process. In the monitoring process, the third calculating section 43 is caused to perform the operations of identifying the various hemoglobins, at predetermined timings. Specifically, when it is recognized that the finger 30 is pressed, the process is started, and, at each elapse of a predetermined time period, the third calculating section 43 is caused to identify the concentrations of the various hemoglobins.

According to the configuration, the condition of the peripheral circulation of the subject can be continuously monitored. This assists to check the effect of treatment with oxygen inhalation for a patient with, for example, carbon monoxide poisoning. This will be described with reference to FIG. 5.

As shown in (a) of FIG. 5, the finger 30 to which the probe 20 is attached includes arterial blood Ba, venous blood Bv, and non-blood tissue Ts. When the finger 30 in this state is pressed, as shown in (b) of FIG. 5, the non-blood tissue Ts is compressed, and arterial blood Ba and venous blood Bv are eliminated. When the pressing is released, as shown in (c) of FIG. 5, arterial blood Ba first starts to flow in, and the thickness of the non-blood tissue Ts begins to return to the original value. As shown in (d) of FIG. 5, then, venous blood Bv starts to flow in. In FIG. 5, (e) shows a situation where the thicknesses of arterial blood Ba, venous blood Bv, and the non-blood tissue Ts return to the states which are attained before the start of the pressurization.

After the pressing is released, as the thickness of the finger 30 returns to the original value, the light attenuation becomes larger. The change of the light attenuation contains components respectively contributed by thickness changes of arterial blood Ba, venous blood Bv, and the non-blood tissue Ts. In the above-described technique, the concentrations of the in-blood substances can be identified while eliminating the influence caused by the change of the non-blood tissue Ts. At the timing shown in (c) of FIG. 5, arterial blood Ba mainly flows in the non-blood tissue Ts. As venous blood Bv flows in as shown in (d) and (e) of FIG. 5, the component contributed by venous blood Bv becoming larger in the light attenuation. With respect to the concentration of abnormal hemoglobin, that of the dye administered to the blood, and the like, however, there is no difference between arterial blood Ba and venous blood Bv.

According to the configuration of the embodiment, the values of the concentrations of the in-blood substances at an arbitrary timing can be identified. For example, the amounts of received light which are measured at the timing shown in (a) of FIG. 5 are set as the reference values (Io1, Io2, Io3, and Io4 in Expressions (1) to (4)), and those of received light which are measured at the timing shown in (b) of FIG. 5 are deemed to have I1, I2, I3, and I4 in the expressions. Then, it possible to measure the concentrations of the in-blood substances of the blood which is eliminated by the pressurization. The change in light attenuation which is calculated from measurement values that, while setting the amounts of received light measured at the timing shown in (b) of FIG. 5 as the reference values, are acquired at a subsequent arbitrary timing can be deemed to be substantially caused by a change in thickness of blood only. Therefore, more accurate monitoring of the concentrations of the in-blood substances can be continuously performed.

The monitoring section 44 acquires differential values of the blood-derived light attenuations Ab21, Ab23, Ab24 which are obtained by the second calculating section 42, thereby performing the determination that the finger 30 is pressed. When the light attenuations Ab21, Ab23, Ab24 are rapidly raised because of pressurization of the finger 30, the differential values are largely changed. When blood is evacuated from the place to which pressurization is applied, the light attenuations Ab21, Ab23, Ab24 have a substantially constant value in the vicinity of the maximum value, and therefore the differential values drift around zero. When the initial large change of the differential values is detected, it is recognized that the living tissue is pressed, and, at a timing when the differential values then begin to drift in the vicinity of zero, it is determined that blood is eliminated. This is used as a trigger for starting the measurement.

When performing a simple work of attaching the probe 20 for pulse oximetry in which measurement is conducted by using four or more wavelengths, to the finger 30 of the subject, and pressing the finger 30 through the probe 20A, therefore, a medical person can measure the concentrations of the in-blood substances of the fingertip at the timing of pressing, and moreover can monitor the subsequent temporal change. When the monitoring is performed while comparing the concentrations of the in-blood substances with the arterial oxygen saturation (SpO2) which can be similarly acquired by the probe 20, it is possible to know a change in condition of the peripheral circulation of a patient with, for example, carbon monoxide poisoning.

The foregoing description of the embodiment has been made in order to facilitate understanding of the presently disclosed subject matter, and is not intended to limit the presently disclosed subject matter. It is a matter of course that the presently disclosed subject matter may be changed or improved without departing the spirit thereof, and includes equivalents thereof.

The light receiver 22 is not always required to be placed at a position where the light beams which have been passed through the finger 30 can be received. Alternatively, a configuration may be employed where the light receiver is placed at a position where light beams which have been reflected from the finger 30 are received, and the light attenuations are acquired based on the reflection intensities of light beams of different wavelengths.

The living tissue to which the probe 20 is to be attached is not limited to the finger 30. Any kind of living tissue may be selected as the object as far as the desired measurement can be performed. For example, the earlobe may be used as the object.

As described above, the reference value of the amounts of received light is obtained by means of pressurization of the finger 30, thereby enabling a subsequent measurement of the concentrations of the in-blood substances to be continuously performed. When the positional relationships of the probe 20 and the living tissue are lost during the measurement, however, the measurement cannot be correctly performed unless the reference value is updated. Therefore, the pressurization is periodically performed, and the reference value is continued to be updated, whereby the reliability of the measurement can be improved. Consequently, the monitoring section 44 may be configured so as to, at each elapse of a predetermined time period, visibly or audibly notify the timing of pressurization through the outputting section 14. When a medical person presses the finger 30 in accordance with the notification, it is possible to surely perform identification of the concentrations of the in-blood substances.

In the acquisition of changes of the amounts of the received light caused by pressing of the finger 30, the intensities of the received light at the pressing, and those after the release of the pressurization may be compared with each other, or the intensities of the received light before the pressing, and those at the pressing may be compared with each other.

As one of effects of the presently disclosed subject matter, the unnecessity of preparation of a special probe in the case where the concentrations of the in-blood substances are to be identified has been described. This is not intended to inhibit the use of additional equipment. A configuration may be employed where, as indicated by the broken lines in FIG. 1, a cuff 50 (an example of the pressurizing section) which covers the probe 20 is attached to the finger 30 of the subject, and the controlling section 12 further includes a cuff pressure controlling section 46 (an example of the pressurization controlling section) which controls the air pressure inside the cuff 50.

The cuff pressure controlling section 46 first pressurizes the interior of the cuff 50 so that the cuff 50 can press the finger 30 of the subject at a predetermined pressure through the probe 20. After elapse of a predetermined time period, the interior of the cuff 50 is depressurized. According to the configuration, the pressurization can be always performed under constant conditions irrespective of the operator or the repeat number. Therefore, the concentrations of in-blood substances can be identified more correctly.

Figure 6:
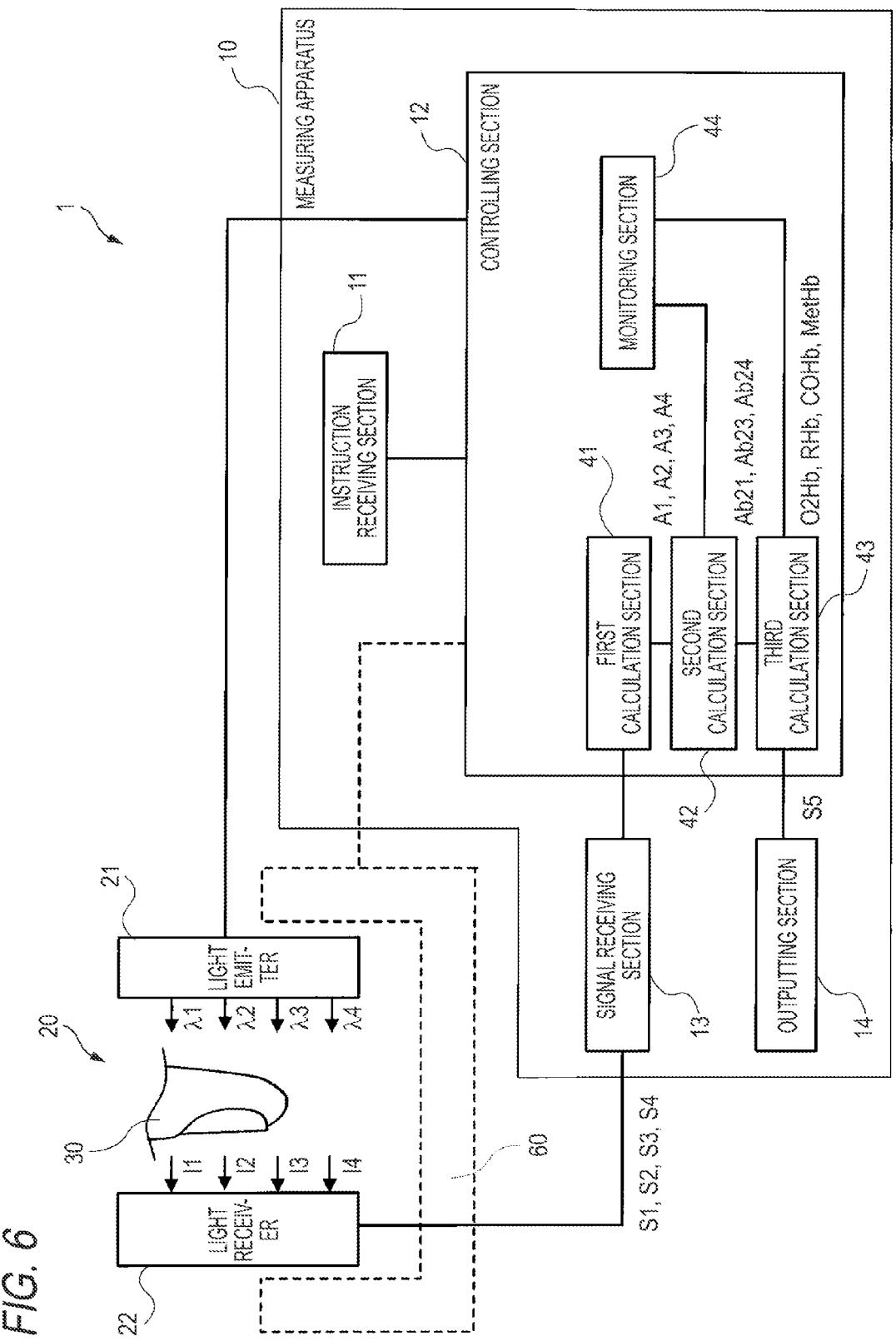
FIG. 6 is a functional block diagram showing the configuration of a biological signal measuring system of a modification.

As shown in FIG. 6, a pressure detecting section 60 may be disposed in the probe 20. In this case, the pressure detecting section 60 detects the pressing of the finger 30 performed by the medical person, and supplies a signal corresponding to the pressure to the controlling section 12. The controlling section 12 is configured so as to calculate the concentrations of in-blood substances corresponding to the signal. According to the configuration, a control is enabled in which a control can be performed in consideration of a difference in pressing degree due to medical persons.

The identified concentrations of the in-blood substances are not always required to be displayed on the displaying device of the outputting section 14 in the form of numerals. In addition to or in place of this, colors or symbols indicative of the concentrations of the in-blood substances may be displayed on the displaying device of the outputting section 14. Alternatively, the outputting section 14 may output sounds indicative of the concentrations of the in-blood substances.

The functions of the first to third calculating sections 41, 42, 43, monitoring section 44, and cuff pressure controlling section 46 which are described above can be realized by the operation of hardware such as circuit devices, that of software such as programs stored in the computer-readable recording medium or in the controlling section 12 which is an example of the computer, or a combination of these operations.

According to an aspect of the presently disclosed subject matter, there is provided a biological signal measuring system comprising: a light emitter which is configured to emit light beams having different N kinds of wavelengths, where N is an integer of four or more; a light receiver which is configured to output N kinds of signals respectively in accordance with received light intensities of the N kinds of light beams that have been passed through or reflected from a living tissue of a subject; a first calculating section which is configured to acquire N kinds of light attenuations based on the N kinds of signals; a second calculating section which is configured to acquire (N−1) kinds of blood-derived light attenuations based on two light attenuations related to (N−1) kinds of combinations selected from the N kinds of light attenuations; a third calculating section which is configured to identify concentrations of (N−1) kinds of in-blood substances based on the (N−1) kinds of blood-derived light attenuations; and an outputting section which is configured to output the identified concentrations.

According to an aspect of the presently disclosed subject matter, there is provided a biological signal measuring apparatus comprising: a signal receiving section which is configured to receive N kinds of signals corresponding to light intensities of light beams that have been passed through or reflected from a living tissue of a subject and that have N kinds of wavelengths, where N is an integer of four or more; a first calculating section which is configured to acquire N kinds of light attenuations based on the N kinds of signals; a second calculating section which is configured to acquire (N−1) kinds of blood-derived light attenuations based on two light attenuations related to (N−1) kinds of combinations selected from the N kinds of light attenuations; a third calculating section which is configured to identify concentrations of (N−1) kinds of in-blood substances based on the (N−1) kinds of blood-derived light attenuations; and an outputting section which is configured to output the identified concentrations.

According to an aspect of the presently disclosed subject matter, there is provided a method of controlling a biological signal measuring apparatus comprising a signal receiving section which is configured to receive N kinds of signals corresponding to light intensities of light beams that have been passed through or reflected from a living tissue of a subject and that have N kinds of wavelengths, where N is an integer of four or more, the method comprising: acquiring N kinds of light attenuations based on the N kinds of signals; acquiring (N−1) kinds of blood-derived light attenuations based on two light attenuations related to (N−1) kinds of combinations selected from the N kinds of light attenuations; identifying concentrations of (N−1) kinds of in-blood substances based on the (N−1) kinds of blood-derived light attenuations, and outputting the identified concentrations.

According to an aspect of the presently disclosed subject matter, there is provided a program causing a computer to execute the method.

According to an aspect of the presently disclosed subject matter, there is provided a non-transitory computer-readable recording medium storing a program causing a computer to execute the method.

When the (N−1) kinds of blood-derived light attenuations are acquired by using the N kinds of frequencies, only relationships between the absorption coefficients and the concentrations of the in-blood substances can be extracted, and the concentrations can be identified. In order to obtain the determination result, the operator is requested only to perform a substantial work of attaching a probe for pulse oximetry in which measurement is conducted by using, for example, four or more wavelengths, to the living issue of the subject. Although it is not required to prepare a special probe and perform a special work, the concentrations of the in-blood substances can be rapidly identified by using a multi-wavelength pulse oximeter.

Each of the blood-derived light attenuations may be acquired based on a difference of the two light attenuations. Two wavelengths corresponding to the two light attenuations which are used for acquiring the difference may be selected as wavelengths in which a difference of light attenuations of non-blood tissue is smaller, from the N kinds of wavelengths. In this case, the concentrations of the in-blood substances can be identified more correctly.

The difference may be obtained by multiplying by a coefficient corresponding to the light attenuation of non-blood tissue in the corresponding wavelength.

When the coefficient is adequately selected, the wavelength dependency of the light attenuation of the non-blood tissue can be eliminated, and the concentrations of the in-blood substances can be identified more correctly.

The N may be four, and the in-blood substances may be three kinds selected from oxygenated hemoglobin, reduced hemoglobin, carbon monoxide hemoglobin, and methemoglobin. The N may be five, and the in-blood substances may be oxygenated hemoglobin, reduced hemoglobin, carbon monoxide hemoglobin, and methemoglobin.

A monitoring section which is configured to cause the third calculating section to identify the concentrations at a predetermined timing, may further provided.

In this case, the peripheral circulation state of the subject can be continuously monitored. This will be of assistance to know the condition of, for example, a patient with carbon monoxide poisoning.

The monitoring section may notify a timing when the living tissue is to be pressed, through the outputting section. In this case, the light attenuations are acquired based on changes of the received light intensities due to pressing of the living tissue.

A pressure detecting section which is configured to detect a pressure applied to the living tissue, and which is configured to output a signal corresponding to the pressure, may further provided.

In this case, a control is enabled which is performed in consideration of a difference in pressing degree due to medical persons.

In order to correctly identify the concentrations of the in-blood substances, it is desirable to press the living tissue each time. According to the configuration, the operator is required only to perform pressurization based on the notification, and therefore identification of the concentrations of the in-blood substances can be surely performed.

A pressurizing section which is adapted to be attached to the subject so as to pressurize the living tissue; and a pressurization controlling section which is configured to control the pressurizing section for causing changes of light attenuations of the living tissue, may further provided.

In this case, the identification of the concentrations of the in-blood substances can be automatized irrespective of the operator of a measuring apparatus or the number of repeated measurements.

What is claimed is:
1. A biological signal measuring system comprising:
   a light emitter which is configured to emit light beams to a living tissue of a subject, the light beams having different N kinds of wavelengths, where N is an integer of four or more;
   a light receiver which is configured to output N kinds of signals respectively in accordance with received light intensities of the N kinds of light beams that have been passed through or reflected from the living tissue of the subject;
   a first calculating section which is configured to acquire N kinds of light attenuations based on the N kinds of signals;
   a second calculating section which is configured to acquire (N−1) kinds of blood-derived light attenuations based on two light attenuations related to (N−1) kinds of combinations selected from the N kinds of light attenuations;

a third calculating section which is configured to identify concentrations of (N−1) kinds of in-blood substances based on the (N−1) kinds of blood-derived light attenuations; and an outputting section which is configured to output the identified concentrations, wherein the light attenuations are acquired based on changes of the received light intensities of a first timing during pressurization in which a pressure is applied to the living tissue and of a second timing before the pressurization or after release of the pressurization, wherein the pressure substantially eliminates both arterial and venous blood from the living tissue.

2. The biological signal measuring system according to claim 1, wherein the second calculating section acquires each of the blood-derived light attenuations based on a difference of the two light attenuations.

3. The biological signal measuring system according to claim 2, wherein two wavelengths corresponding to the two light attenuations which are used for acquiring the difference are selected as wavelengths in which a difference of light attenuations of non-blood tissue is smaller, from the N kinds of wavelengths.

4. The biological signal measuring system according to claim 2, wherein the difference is obtained by multiplying by a coefficient corresponding to the light attenuation of non-blood tissue in the corresponding wavelength.

5. The biological signal measuring system according to claim 1, wherein the N is four, and the in-blood substances are three kinds selected from oxygenated hemoglobin, reduced hemoglobin, carbon monoxide hemoglobin, and methemoglobin.

6. The biological signal measuring system according to claim 1, wherein the N is five, and the in-blood substances are oxygenated hemoglobin, reduced hemoglobin, carbon monoxide hemoglobin, and methemoglobin.

7. The biological signal measuring system according to claim 1, further comprising a monitoring section which is configured to cause the third calculating section to identify the concentrations at a predetermined timing.

8. The biological signal measuring system according to claim 7, wherein the monitoring section notifies a timing when the living tissue is to be pressed, through the outputting section.

9. The biological signal measuring system according to claim 7, further comprising:
a pressurizing section which is adapted to be attached to the subject so as to pressurize the living tissue; and
a pressurization controlling section which is configured to control the pressurizing section for causing changes of light attenuations of the living tissue.

10. The biological signal measuring system according to claim 1, further comprising a pressure detecting section which is configured to detect the pressure applied to the living tissue, and which is configured to output a signal corresponding to the pressure.

11. The biological signal measuring system according to claim 1, wherein
the pressure is applied to the living tissue located between the light emitter and the light receiver.

12. A biological signal measuring apparatus comprising:
a signal receiving section which is configured to receive N kinds of signals corresponding to light intensities of light beams that have been passed through or reflected from a living tissue of a subject and that have N kinds of wavelengths, where N is an integer of four or more;
a first calculating section which is configured to acquire N kinds of light attenuations based on the N kinds of signals;
a second calculating section which is configured to acquire (N−1) kinds of blood-derived light attenuations based on two light attenuations related to (N−1) kinds of combinations selected from the N kinds of light attenuations;
a third calculating section which is configured to identify concentrations of (N−1) kinds of in-blood substances based on the (N−1) kinds of blood-derived light attenuations; and
an outputting section which is configured to output the identified concentrations, wherein the light attenuations are acquired based on changes of the received light intensities of a first timing during pressurization in which a pressure is applied to the living tissue and of a second timing before the pressurization or after release of the pressurization, and
wherein the pressure substantially eliminates both arterial and venous blood from the living tissue.

13. The biological signal measuring apparatus according to claim 12, wherein
the pressure is applied to the living tissue located between a light emitter configured to emit the light beams and a light receiver configured to output the N kinds of signals.

14. A method of controlling a biological signal measuring apparatus comprising a signal receiving section which is configured to receive N kinds of signals corresponding to light intensities of light beams that have been passed through or reflected from a living tissue of a subject and that have N kinds of wavelengths, where N is an integer of four or more, the method comprising:
acquiring N kinds of light attenuations based on the N kinds of signals;
acquiring (N−1) kinds of blood-derived light attenuations based on two light attenuations related to (N−1) kinds of combinations selected from the N kinds of light attenuations;
identifying concentrations of (N−1) kinds of in-blood substances based on the (N−1) kinds of blood-derived light attenuations, and
outputting the identified concentrations,
wherein the light attenuations are acquired based on changes of the received light intensities of a first timing during pressurization in which a pressure is applied to the living tissue and of a second timing before the pressurization or after release of the pressurization, and
wherein the pressure substantially eliminates both arterial and venous blood from the living tissue.

15. A non-transitory computer-readable storage medium storing a program causing a computer to execute the method according to claim 14.

16. The method according to claim 14, wherein
the pressure is applied to the living tissue located between a light emitter configured to emit the light beams and a light receiver configured to output the N kinds of signals.

* * * * *